United States Patent
Framroze

(10) Patent No.: US 10,981,868 B1
(45) Date of Patent: Apr. 20, 2021

(54) SINGLE STEP REGIOSELECTIVE CYCLIZATION AND CHLORINATION OF HYDROXYAMINO-N-(2-METHYLPHENYL) ACETAMIDE TO 5-CHLORO-7-METHYLINDOLINE-2,3-DIONE

(71) Applicant: Tagros Chemicals India Pvt. Ltd., Chennai (IN)

(72) Inventor: Bomi P Framroze, Portola Valley, CA (US)

(73) Assignee: Tagros Chemicals India Pvt. Ltd., Chennai (IN)

( * ) Notice: Subject to any disclaimer, the term of this patent is extended or adjusted under 35 U.S.C. 154(b) by 0 days.

(21) Appl. No.: 16/992,034

(22) Filed: Aug. 12, 2020

(51) Int. Cl.
*C07D 209/38* (2006.01)

(52) U.S. Cl.
CPC .................... *C07D 209/38* (2013.01)

(58) Field of Classification Search
CPC .................................................... C07D 209/38
See application file for complete search history.

(56) References Cited

FOREIGN PATENT DOCUMENTS

CN          103058993     *   4/2013   ........... C07D 401/04

* cited by examiner

*Primary Examiner* — Alicia L Otton

(57) ABSTRACT

A one-pot process for the manufacture of 5-chloro-7-methylindoline-2,3-dione starting from 2-hydroxyimino-N-(2-methylphenyl)acetamide via tandem cyclization in sulfuric acid and acetic acid, followed by in-situ chlorination with sulfur dioxide and chlorine gas in high regioselectivity and yield.

5 Claims, No Drawings

SINGLE STEP REGIOSELECTIVE CYCLIZATION AND CHLORINATION OF HYDROXYAMINO-N-(2-METHYLPHENYL) ACETAMIDE TO 5-CHLORO-7-METHYLINDOLINE-2,3-DIONE

FIELD

This invention relates to a one-pot process for the manufacture of 5-chloro-7-methytindoline-2,3-dione starting from 2-hydroxyimino-N-(2-methylphenyl)acetamide. Initial cyclization is carried out in a mixture of sulfuric acid and acetic acid, followed by reaction with sulfur dioxide and chlorine gas to directly yield 5-chloro-7-methylindoline-2,3-dione in high regioselectivity and yield.

BACKGROUND 5-chloro-7-methylindoline-2,3-dione can be a potential intermediate compound in the manufacture of the agrochemical insecticide, chlorantraniliprole. The synthesis of chlorantraniliprole has been described in U.S. Pat. No. 7,232,836 using a synthetic route that does not use 5-chloro-7-methylindoline-2,3-dione as an intermediate compound. Several other publications describe other synthetic routes to chlorantraniliprole. none of which describe the synthesis of 5-chloro-7-methyl indole-2,3-dione or its use as an intermediate. (U.S. Pat. Nos. 7,528,260, 8,153,844, 8,217,179, 8,481,744, 8,871,939, 9,162,973, WO2018214685).

The desired 5-chloro-7-methylindoline-2,3-dione may be made by two routes: Route 1-chlorination of N-(2-methylphenyl)acetamide by cyclization to produce the desired 5-chloro-7-methylindoline-2,3-dione or Route 2 by the cyclization of the un-chlorinated N-(2-methylphenyl)acetamide to yield the 7-methylindoline-2,3-dione which is subsequently chlorinated at the 5-position to yield the desired 5-chloro-7-methylindoline-2,3-dione.

With reference to Route 1, the prior art has described a few methods to chlorinate N-(o-acyl) acetamides in general. Chenevert, Robert and Ampleman et al (*Canadian Journal of Chemistry*, v65(2), p307-10) have reported the chlorination of N-(2-methylphenyl)acetamide using $Cl_2$ gas, with a poor regioselectivity of 61% for the desired N-(4-chloro-2-methylphenyl)acetamide. Singh, Harshvardhan et al (*European Journal of Organic Chemistry* v34, 4748-4753; 2018) and Bovonsombat, Pakom et al (*Tetrahedron*, 73(46), 6564-6572; 2017) have reported the chlorination of N-(o-acyl) acetamides using N-Chlorosuccinimide with similar low regioselectivity. Other reagents such as N-Chloro-4-hydroxy-2,2,6,6-tetramethylpiperidine, t-butylhypochlorite and hydrochloric acid with hydrogen peroxide have also been described without achieving the desired regioselectivity needed. (V. P. et al; *Russian Journal of Applied Chemistry* v77(6), 964-967; 2004; Lengyel, Istvan et al; *Synthetic Communications* v28(10), 1891-1896; 1998; Pan, Qiangbiao et al. CN 107021889)

We carried out chlorination of N-(2-methylphenyl)acetamide in acetic acid using chlorine gas As shown in Example 1, this results in a low yield reaction with multiple regioisomeric byproducts that makes the isolation of the desired N-(4-chloro-2-methylphenyl) acetamide very low yielding and environmentally wasteful. Further, as shown in Example 2, chlorination of the downstream 2-(hydroxyimino)-N-(o-tolyl)acetamide intermediate as another pre-cyclization option actually does not lead to any isolable quantity of the desired N-(4-chloro-2-methylphenyl)acetamide at all. Thus as shown above as Route 1, chlorination of N-(2-methylphenyl)acetamide is not a viable route to the desired 5-chloro-7-methylindole-2,3-dione.

The second method, Route 2 involves chlorination of the 7-methylindoline-2,3-dione, after cyclization of the N-(2-methylphenyl)-2-(hydroxyimino)acetamide. The prior art describes some general methods of chlorination of indoline-2,3-diones. Gutierrez, Elisa et al (e-EROS *Encyclopedia of Reagents for Organic Synthesis*, 1-5, 2013) have reported the chlorination of indoline-2,3-dione using sodium dichloroisocyanurate. Hiegel, Gene A. et al (e-EROS *Encyclopedia of Reagents for Organic Synthesis*, 1-7; 2013) have reported the chlorination of indoline-2,3-dione using Isocyanuric chloride. Mahajan, Tanu et al (*Industrial & Engineering Chemistry Research*, 51(10), 3881-3886, 2012) have reported the chlorination of indoline-2,3-dione using N-chlorosuccinimide while Dos Santos, Edeilza Lopes et al, (*Journal of Molecular Catalysis A: Chemical*, 295(1-2), 18-23; 2008) have reported the use of isatin carbonimidic dichloride and Li, Wei et al (CN103058993) have reported the use of $SO_2Cl_2$ in the presence of $Ac_2O$. Further as shown in Example 3, direct chlorination of 7-methylindoline-2,3-dione with chlorine gas in acetic acid results once again in poor regioselectivity that requires expensive fractionational distillation for purification to the desired 95%+ regioselectivity for use in the manufacture of chlorantraniliprole.

Consequently there still exists a need for a commercially viable method to regioselectively add a chlorine atom at the 5-position of indoline-2,3-diones and specifically to 7-methylindoline-2,3-dione to produce the key agrochemical intermediate, 5-chloro-7-methylindole-2,3-dione, in good yield and with the high regioselectivity that would allow for direct, without fractional distillation, use in the manufacture of chlorantraniliprole.

SUMMARY OF THE INVENTION

The present invention describes a sequential cyclization and chlorination of 2-hydroxyimino-N-(o-tolyl)acetamide that is regioselective and high yielding for preparing 5-chloro-7-methylindoline-2,3-dione by reacting 2-hydroxyimino-N-(o-tolyl)acetamide with a mixture of concentrated sulfuric acid and acetic acid at 50-60° C. for 30 minutes followed by sequential addition of sulfur dioxide and chlorine gas directly into the reaction mixture and heating until the 5-chloro-7-methylindoline-2,3-dione is formed. The presence of the sulfuric acid and acetic acid in a 2:1 volumetric ratio is a necessary and unexpected reaction condition that is required to ensure the rapid formation of the cyclized 7-methylindoline-2,3-dione and to simultaneously allow for the direct regioselective chlorination at the 5-position of the intermediate 7-methylindoline-2,3-dione, without its isolation. This results in a high yielding and highly regioselective process while absence of either the sulfuric acid or the acetic acid leads to little to zero 5-chloro-7-methylindole-2,3-dione formation.

Thus the method described herein uses the hitherto unknown co-addition of acetic acid and sulfuric acid during the initial cyclization of 2-hydroxyimino-N-(o-tolyl)acetamide to facilitate an in situ addition of sulfur dioxide and chlorine gas to chlorinate, without isolation, the 7-methylindoline-2,3-dione formed and subsequently isolate, in excellent yields and regioselective purity, the desired 5-chloro-7-methylindoline-2,3-dione solid powder.

This new method also eliminates (i) the isolation of the intermediate 7-methylindoline-2,3-dione with commensurate loss of yield and (ii) the unwanted production of undesired chloro regioisomers that would require fractional distillation before use.

DETAILED DESCRIPTION OF THE INVENTION

Before describing the present invention in detail, it is to be understood that the terminology used herein is for the purpose of describing particular embodiments only, and is not intended to be limiting.

In accordance with the present invention, there is provided a process to produce, in a highly regiospecific and cost effective manner, the agrochemical intermediate 5-chloro-7-methylindoline-2,3-dione.

In one embodiment of the present invention, a process is described for the preparation of 5-chloro-7-methylindoline-2,3-dione by reacting 1.0 equivalent of 2-hydroxyimino-N-(o-tolyl)acetamide dissolved in 2.0 equivalent of acetic acid with 4.0 equivalent of sulfuric acid at 55° C. followed by addition of 0.3 equivalent sulfur dioxide and 1.5 equivalent chlorine gas and heating the mixture to 65° C. for 2 hours. The reaction mass is added to 10.0 equivalent of ice water, stirred and filtered to yield the desired 5-chloro-7-methyl-indoline-2,3-dione in high yield and purity.

It will be clear to those skilled in the art that modifications can be made to the process described herein without departing from the inventive concept set forth in our claims below.

Example 1

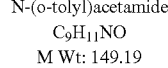

N-(o-tolyl)acetamide
$C_9H_{11}NO$
M Wt: 149.19

N-(4-chloro-methylphenyl)acetamide
$C_9H_{10}ClNO$
M Wt: 183.63

70 g of N-(o-tolyl)acetamide is dissolved in 300 ml of acetic acid and this mixture was taken in 500 ml of RBF. This mixture was cooled to 25° C., and 50 g of chlorine purged to mass. Reaction mass was gradually heated to reflux temperature for 2 hr. After completing the reaction acetic acid was distilled out and quenched with water to get 25 g (50% GC yield) of N-(4-chloro-2-methylphenyl)acetamide.

Example 2

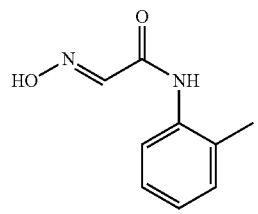

2-(hydroxyimino)-N-(o-tolyl)acetamide
$C_9H_{10}N_2O_3$
M Wt: 178.19

-continued

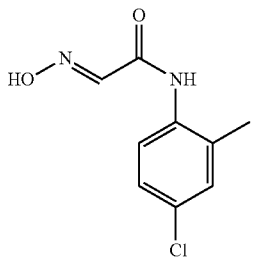

N-(4-chloro-2-methylphenyl)-2-(hydroxyimino)acetamide
$C_9H_9ClN_2O_2$
M Wt: 212.63

15 g of 2-(hydroxyimino)-N-(o-tolyl)acetamide was dissolved in 150 ml of acetic acid and this mixture was taken in 250 ml of RBF. This mixture was cooled to 25° C., and 50 g of chlorine purged to mass. Reaction mass was gradually heated to reflux temperature for 2 hr, reaction mass was monitored by HPLC, and found formation of more impurities.

Example 3

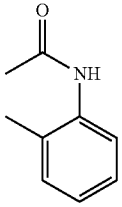

7-methylindoline-2,3-dione
$C_9H_7NO_2$
M Wt: 161.16

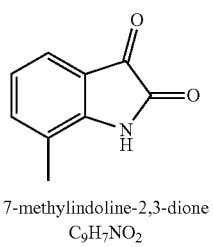

5-chloro-7-methylindoline-2,3-dione
$C_9H_6ClNO_2$
M Wt: 195.60

29.4 g (0.2 mole) of 7-methyl isatin was dissolved in 2220 ml of acetic acid and this mixture was taken into a kettle and was cooled to 25° C. 28 g of chlorine was purged into the kettle and the reaction mass was slowly heated to reflux condition and maintained for 3 hr. Reaction was monitored by HPLC method, reaction completed with less than 70% of regio-selective product formed.

Example 4

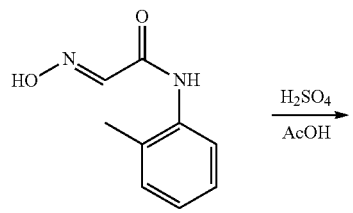

(E)-2-(hydroxyimino)-N-(o-
tolyl)acetamide
C₉H₁₀N₂O₂
M Wt: 178.19

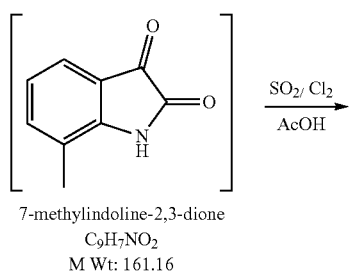

7-methylindoline-2,3-dione
C₉H₇NO₂
M Wt: 161.16

5-chloro-7-methylindoline-2,3-dione
C₉H₆ClNO₂
M Wt: 195.6

39.2 g (0.4 mole) of concentrated sulphuric acid was taken into a RBF, heated to 50-60° C. 17.8 g of (0.1 mole) of 2-(hydroxyimino)-N-(o-tolyl)acetamide was dissolved in 20 ml of acetic acid at hot condition and this solution was slowly added to the reaction mass over the period of 20-30 mins. After completion of this stage the mass was cooled to room temperature. 0.03 mole of sulphur dioxide was purged into reaction mass followed by addition of 0.15 mole of chlorine gas into reaction mass. This reaction mixture was heated to 60-65° C. and cooking for 2 hr. After completion of reaction, mass was quenched in ice cool water. The precipitated solid was filtered and dried to yield 15 g (77% of yield) of 5-chloro-7-methylindoline-2,3-dione and 98% regioselectivity.

Example 5

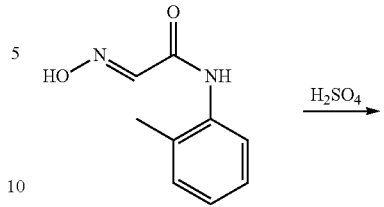

(E)-2-(hydroxyimino)-N-(o-
tolyl)acetamide
C₉H₁₀N₂O₂
M Wt: 178.19

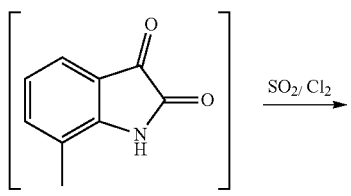

7-methylindoline-2,3-dione
C₉H₇NO₂
M Wt: 161.16

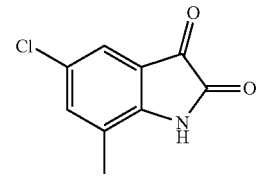

5-chloro-7-methylindoline-2,3-dione
C₉H₆ClNO₂
M Wt: 195.6

39.2 g (0.4 mole) of concentrated sulphuric acid was taken into RBF and then heated to 50-60° C. 17.8 g of (0.1 mole) of 2-(hydroxyimino)-N-(o-tolyl)acetamide was added slowly into reaction mass over the period of 20-30 mins. After completion, the mass is cooled to room temperature. Reaction mass became thick and started purging of SO₂ gas followed by Cl₂ gas. There was no reaction observed.

What is claimed is:
1. A process that reacts 2-hydroxyimino-N-(o-tolyl) acetamide with a mixture of sulfuric acid and acetic acid followed by reaction with sulfur dioxide and chlorine gas to yield 5-chloro-7-methylindoline-2,3-dione.
2. A process according to claim 1 wherein the sulfuric acid is between 18M and 18.4M concentration.
3. A process according to claim 1 wherein the acetic acid is between 17M and 17.4M concentration.
4. A process according to claim 1, wherein the volumetric ratio of sulfuric acid to acetic acid is 2:1.
5. A process according to claim 1, wherein the reaction temperature of the sulfuric acid and acetic acid is between 50 and 60° C.

\* \* \* \* \*